(12) United States Patent
Bragd et al.

(10) Patent No.: US 8,143,472 B1
(45) Date of Patent: Mar. 27, 2012

(54) ABSORBENT STRUCTURE IN AN ABSORBENT ARTICLE AND A METHOD OF PRODUCING IT

(75) Inventors: Petter Bragd, Stenhuggarevägen (SE); Shabira Abbas, Kåserigatan (SE); Andrea Schmid, Sjökullevägen (SE)

(73) Assignee: SCA Hygiene Products AB, Gothenburg (SE)

( * ) Notice: Subject to any disclaimer, the term of this patent is extended or adjusted under 35 U.S.C. 154(b) by 1662 days.

(21) Appl. No.: 09/651,127

(22) Filed: Aug. 30, 2000

Related U.S. Application Data

(60) Provisional application No. 60/198,453, filed on Apr. 19, 2000.

(30) Foreign Application Priority Data

Aug. 30, 1999 (SE) ...................................... 9903070

(51) Int. Cl.
*A61F 13/15* (2006.01)
(52) U.S. Cl. .................. 604/369; 604/378; 604/379
(58) Field of Classification Search .................. 604/368, 604/369, 378, 379
See application file for complete search history.

(56) References Cited

U.S. PATENT DOCUMENTS

| | | | |
|---|---|---|---|
| 3,122,140 A | 2/1964 | Crowe, Jr. | |
| 3,301,257 A | 1/1967 | Crowe, Jr. et al. | |
| 3,512,530 A | 5/1970 | Jones | |
| 3,545,441 A | 12/1970 | Gravdahl | |
| 3,598,742 A | 8/1971 | Jamison et al. | |
| 4,104,435 A | 8/1978 | Ballesteros | |
| 4,239,043 A | 12/1980 | Gellert | |
| 4,394,930 A | 7/1983 | Korpman | |
| 4,902,565 A | 2/1990 | Brook | |
| 4,957,810 A | 9/1990 | Eleouet et al. | |
| 4,985,467 A | 1/1991 | Kelly et al. | |
| 5,147,345 A | 9/1992 | Young et al. | |
| 5,260,345 A | 11/1993 | DesMarais et al. | |
| 5,338,766 A | 8/1994 | Phan et al. | |
| 5,506,035 A | 4/1996 | Van Phan et al. | |
| 5,550,189 A | 8/1996 | Qin et al. | |
| 5,713,881 A * | 2/1998 | Rezai et al. ................... | 604/365 |
| 5,718,916 A | 2/1998 | Scherr | |
| 5,728,083 A * | 3/1998 | Cohen et al. .................. | 156/296 |
| 5,785,697 A * | 7/1998 | Trombetta et al. ............ | 604/378 |
| 5,795,921 A | 8/1998 | Dyer et al. | |
| 5,817,081 A | 10/1998 | LaVon et al. | |

(Continued)

FOREIGN PATENT DOCUMENTS

DE 19540951 A1 5/1997

(Continued)

OTHER PUBLICATIONS

Kent Malmgren et al., U.S. Appl. No. 09/651,130, entitled "Absorbent Foam Material and an Absorbent Structure Containing Said Foam Material" filed Aug. 30, 2003.

*Primary Examiner* — Lynne Anderson
(74) *Attorney, Agent, or Firm* — Buchanan Ingersoll & Rooney PC

(57) ABSTRACT

Absorbent structure in an absorbent article such as a diaper, pant diaper, incontinence guard, sanitary napkin, wound dressing, bed protection etc. and comprising a compressed foam material (1) which expands upon wetting, at which the foam material (1) comprises at least two integrated layers (2,3,4) having different mean pore sizes.

11 Claims, 2 Drawing Sheets

U.S. PATENT DOCUMENTS

| | | | |
|---|---|---|---|
| 5,868,724 A * | 2/1999 | Dierckes et al. | 604/367 |
| 5,869,171 A | 2/1999 | Shiveley et al. | |
| 6,033,769 A | 3/2000 | Brueggemann et al. | |
| 6,093,870 A | 7/2000 | Carlsson | |
| 6,103,358 A | 8/2000 | Brüggemann et al. | |
| 6,136,873 A | 10/2000 | Hähnle et al. | |
| 6,191,340 B1 * | 2/2001 | Carlucci et al. | 604/369 |
| 6,261,679 B1 | 7/2001 | Chen et al. | |
| 6,518,479 B1 * | 2/2003 | Graef et al. | 604/383 |
| 6,657,101 B1 | 12/2003 | Malmgren et al. | |
| 6,673,981 B1 | 1/2004 | Strömbom et al. | |

FOREIGN PATENT DOCUMENTS

| | | |
|---|---|---|
| EP | 0 044 624 B1 | 10/1984 |
| EP | 0 293 208 | 11/1988 |
| EP | 0 212 618 B1 | 6/1992 |
| EP | 0 478 011 B1 | 10/1994 |
| EP | 0 747 420 A1 | 12/1996 |
| EP | 0 532 002 B1 | 5/1997 |
| EP | 0 598 833 B1 | 10/1997 |
| EP | 0 804 913 | 11/1997 |
| SE | 9801694-2 | 11/1999 |
| WO | 93/04092 A1 | 3/1993 |
| WO | 94/00512 A1 | 1/1994 |
| WO | 94/22502 A1 | 10/1994 |
| WO | 65/31500 A2 | 11/1995 |
| WO | 96/16624 A2 | 6/1996 |
| WO | 96/21680 | 7/1996 |
| WO | 97/32612 A1 | 9/1997 |
| WO | 98/55540 A1 | 12/1998 |

* cited by examiner

ABSORBENT STRUCTURE IN AN ABSORBENT ARTICLE AND A METHOD OF PRODUCING IT

This application claims the benefit of U.S. Provisional Application No. 60/198,453, filed on Apr. 19, 2000, the entire content of which is hereby incorporated by reference.

TECHNICAL FIELD

The present invention refers to an absorbent structure in an absorbent article such as a diaper, pant diaper, incontinence guard, sanitary napkin, wound dressing, bed protection etc. and comprising a compressed foam material which expands upon wetting. The invention further refers to a method of producing the absorbent structure and an absorbent article containing the absorbent structure according to the invention.

BACKGROUND OF THE INVENTION

Absorbent articles of the above mentioned kind are intended to be used for absorption of body liquids such as urine and blood. They usually comprise a liquid perilous topsheet, which during use is intended to be facing the wearer's body, e g a nonwoven material of spunbond type, a meltblown material, a carded bonded wadding etc. They further have a liquid impervious backsheet, e g a plastic film, a plastic coated nonwoven or a hydrophobic nonwoven, and an absorbent structure arranged between the liquid pervious topsheet material and the liquid impervious backsheet. This absorbent structure may be constructed by several layers such as a liquid acquisition layer, storage layer and distribution layer.

As a liquid acquisition layer there is usually used a porous material having a high momentaneous liquid receiving capacity. Examples of such material are cellulosic fluff pulp of thermomechanic or chemothermomechanic (CTMP) type, chemically stiffened cellulosic fibers, synthetic fiber structures of different types and porous foam materials etc.

As a storage layer there is usually used cellulosic fluff pulp mixed with so called superabsorbents, i e crosslinked polymers with the ability to absorb several times their own weight (10 times or more) of body fluids. It is also possible to use an absorbent foam material as a storage layer. As a distribution layer there can be used cellulosic fluff pulp, tissue layers, foam, synthetic fibers and the like having high liquid distribution capacity. It is also possible to combine two or more of the functions acquisition, storage and distribution in one and the same layer.

It is previously known through U.S. Pat. No. 3,512,450, EP-A-0 293 208 and EP-A-0 804 913 to use a compressed foam material of regenerated cellulose, e g viscose, as an absorbent structure in an absorbent article of the above mentioned kind, e g a sanitary napkin. The article may then be made very thin and still have a high absorption capacity. The compressed viscose foam expands quickly i the z-direction when liquid is absorbed by the material when wetted.

OBJECT AND MOST IMPORTANT FEATURES OF THE INVENTION

The object of the present invention is to improve the function of an absorbent structure in the form of a compressed foam material especially with respect to liquid acquisition- and distribution capacity. This has according to the invention been achieved by the fact that the foam material comprises two integrated layers having different mean pore sizes.

There is further referred to a method of producing an absorbent structure, comprising separately forming at least two different foam materials having different pore sizes and applying the foam materials on top of each other while still not dry, after which the combined material layers are dried and compressed.

There is also referred to an absorbent article such as a diaper, a pant diaper, an incontinence guard, a sanitary napkin, a wound dressing, a bed protection etc. containing an absorbent structure according to the invention.

Further features of the invention are disclosed in the following description and of the claims.

DESCRIPTION OF DRAWINGS

The invention will in the following be closer described with reference to an embodiment shown in the accompanying drawings.

DESCRIPTION OF EMBODIMENTS

Figure 1:
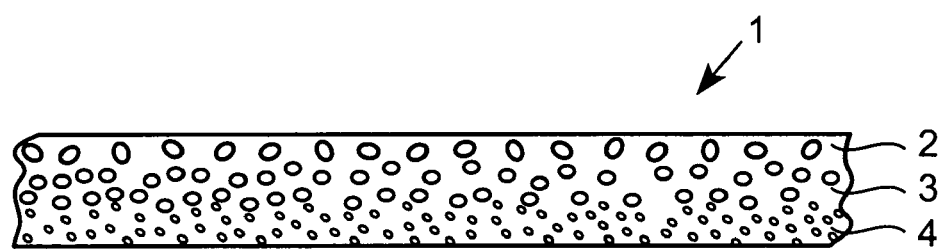
FIG. 1 shows a schematic cross section of an absorbent structure according to the invention in compressed form containing three different integrated layers
Figure 2:
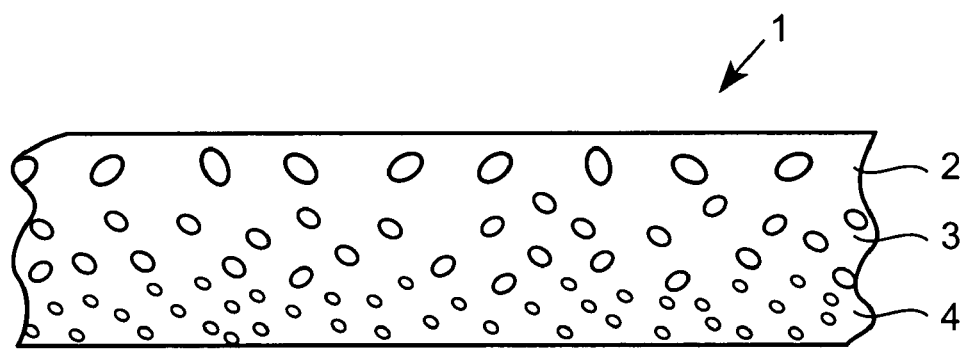
FIG. 2 shows the absorbent structure according to FIG. 1 in expanded form.

The absorbent structure 1 according to the invention comprises at least two, in the embodiment shown in FIGS. 1 and 2 three, integrated layers 2, 3 and 4. Each layer consists of a compressed foam material, which upon contact with liquid expands strongly while absorbing the liquid. The layers have different pore sizes. With pore size is meant the effective means pore size which the material has in expanded condition. The effective means pore size is determined by means of a PVD (Pore Volume Distribution)-apparatus manufactured by Textile Research Institute, Princeton, USA. The function of the PVD-apparatus is described in detail in Miller, B. and Tyomkin, L. Textile Research Journal 56 (1986) 35.

The different layers 2, 3 and 4 are preferably integrated with each other and partly penetrate into each other so that there is no clear partitioning line between the layers but a mixture of the different pore sizes. By this the liquid transport between the layers is promoted.

According to a preferred embodiment the foam material is of regenerated cellulose, such as viscose, which is a foam containing a framework of cellulose. The principle for making a porous viscose foam is known since long ago and shortly takes place in the following way. Cellulose, usually sulphite pulp, is allowed to swell in sodium hydroxide. Carbon disulphide is added at which the cellulose is successively dissolved. In order to improve the mechanical strength in the material for example cotton fibers may be added. To this cellulose solution there is added and dispersed a salt in the form of sodium sulphate. When then the solution is heated the cellulosed is regenerated (the Carbon disulphide is evaporated) and the salt (sodium sulphate) is dissolved by washing the material with water at which a porous spongelike structure is obtained. The material is dried and compressed if desired In order to provide the desired pore size gradient different viscose solutions are used, which are applied on top of each other and then regenerated. Sodium sulphate with different particle sizes is used in the different layers, at which a different pore size of the foam is obtained. By the fact that the different layers are placed on top of each other before they are dry there is achieved an integrated structure, in which the layers partly penetrated into each other. This is verified by PVD measurements which indicate an integrated material with no gape between the different layers.

After regeneration of the cellulose and washing for removing the salt particles the to material is dried and compressed to the desired density, which should be in the interval 0.1 to 2.0 g/cm$^3$. The material will upon liquid absorption expand quickly in volume from 2 to 20 times, preferably from 2 to 15 times its volume in compressed condition. The increase of volume at the absorption mainly occurs in the compression direction, i e in the z-direction of the material.

The material is used in such a way in an absorbent article that the layer having the largest pore size is applied on top, closest to the wearer, so that there will be a decreasing pore size in the direction away from the wearer. By this there will be a good liquid acquisition, due to the large pores in the uppermost layer, and an improved distribution in the underlying layers due to the higher capillary distribution in the layers having the smaller pores. Since liquid due to the higher capillary force of smaller pores tends to be distributed form larger to smaller pores, the distribution of liquid in the z-direction away from the uppermost layer is promoted, at the same time as rewet of liquid from the underlying layers to the upper layer is prevented The foam may of course be of an optional polymeric material and it is possible to create different mean pore sizes of the respective foam layers by other methods than described above by means of salt crystals of different particle sizes. One such alternative way is to use different types of foaming agents when producing the different foam layers, and which provide different mean pore sizes. Another way is to influence the foaming process in such a way, e g by heating the different layers to different degrees during foaming. In this case it would be possible to use the same foaming agent in the different layers.

Superabsorbent materials may be added to the foam material in connection with the viscose production, i e before foaming. The concentration of superabsorbent preferably is in the form of a gradient, so that the layer with the largest pores contains the smallest amount of superabsorbent and the layer with the smallest pores contains the highest amount of superabsorbent. By this the largest liquid storage capacity is provided in the layer facing away from the wearer.

The superabsorbent material may also be applied on the dried foam, e g in the form of a monomer solution which is applied on the side of the which is intended to be facing away from the wearer. The monomer solution will then form a coating on one side of the foam and a part of the monomer solution will penetrate into the open pore system of the foam. The monomer solution is polymerized and is then crosslinked. With this method there is provided a gradient of the superabsorbent concentration from one side of the foam on which the monomer solution has been applied and a distance into the foam material, so far as the monomer solution has penetrated.

The monomer solution can also be in the form of a solution which when applied to the compressed foam runs into the pore system thereof and forms a coating on the pore walls.

The monomer solution may also be in the form of a foamed dispersion, which after application to one side of the compressed foam is polymerized and crosslinked. The advantage of applying the superabsorbent material in the form of a foamed dispersion is that a porous structure is formed also of the superabsorbent material, which promotes the liquid transport.

The foam material in the different layers may also be of different polymers, at which it for example would be possible to provide a hydrophilicity gradient i the z-direction by having foams of different hydrophilicity/hydrophobicity in the different layers.

Figure 3:
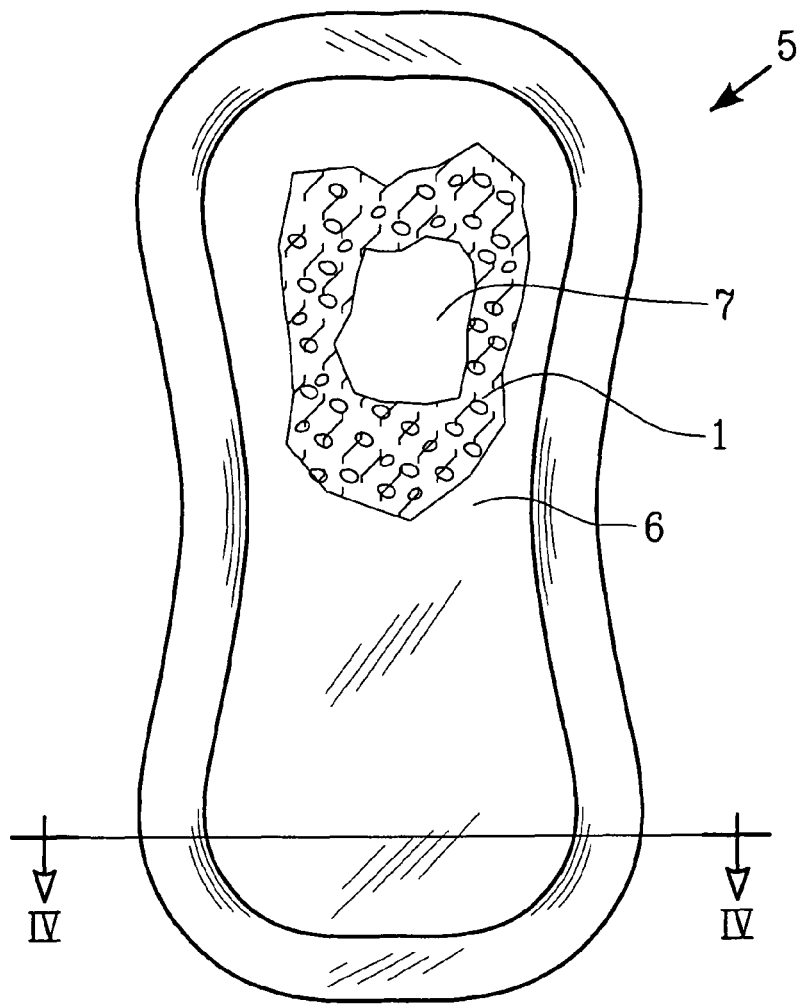
FIG. 3 shows in a view from above an absorbent article in the form of an incontinence guard.
Figure 4:
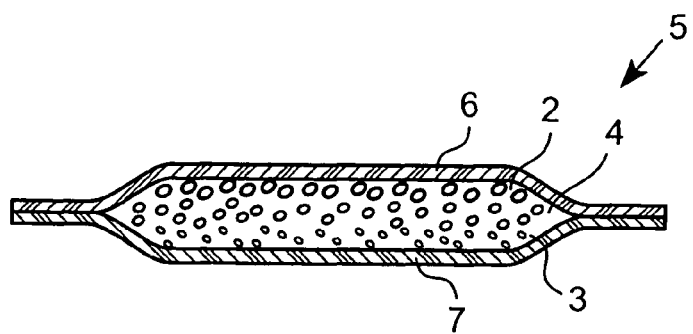
FIG. 4 is a section according to the line IV-IV in FIG. 3 on an enlarged scale.

In FIGS. 3 and 4 there is shown an example of an absorbent article 5 in the form of an incontinence guard comprising a liquid pervious topsheet 6, a liquid impervious backsheet 7 and an absorbent structure 1 according to the invention enclosed therebetween.

The liquid pervious topsheet 6 may comprise a nonwoven material, e g a spunbond material of synthetic filaments, a thermobonded material, e g a bonded carded fibrous material or a perforated plastic film. The liquid impervious backsheet 7 usually consists of a plastic film, a nonwoven material which has been coated with a liquid impervious material or a hydrophobic nonwoven material which resists liquid penetration.

The topsheet 6 and the backsheet 7 have a somewhat larger extension in the plane than the absorbent structure 1 and extend outside the edges thereof. The layers 6 and 7 are interconnected within their projecting portions, e g by gluing or welding with heat or ultrasonic.

Between the topsheet 6 and the absorbent structure 1 there may optionally be arranged a soft and porous liquid acquisition layer.

It is pointed out that the incontinence guard shown in the drawings and described above only is a non-limiting example of an absorbent article. Thus the shape of the article as well as its overall construction may vary. The absorbent article may also be a diaper, a pant diaper, a sanitary napkin, a bed protection or the like. It would also be possible to eliminate the separate liquid pervious topsheet 6 and have the absorbent structure 1 consisting of the foam material according to the invention be directly applied against the skin of the wearer The absorbent structure 1 may also be combined with other absorbent layers, e g of cellulose fluff pulp, superabsorbents and the like, preferably arranged between the absorbent structure 1 and the liquid impervious backsheet 7. As mentioned above a porous and resilient liquid acquisition layer may be applied between the topsheet 6 and the absorbent structure 1.

The absorbent structure 1 according to the invention may also be arranged over only a part of the total surface of the absorbent body of the absorbent article, e g in the intended wetting area of the article where the body liquid will be discharged and which normally is located towards the front part of the article 5. He parts of the absorbent body that are located outside the wetting area may then be of optional other absorbent material

The invention claimed is:

1. An absorbent structure in an absorbent article, the absorbent structure comprising a compressed foam material which expands upon wetting, the foam material comprises at least two integrated layers having different mean pore sizes, wherein the layers are formed by placing one on top of the other before they are dry so that the layers partly penetrate into each other so that there is no clear partitioning line between the layers, wherein the foam material is regenerated cellulose.

2. The absorbent structure as claimed in claim 1, wherein the foam material contains superabsorbent material.

3. The absorbent structure as claimed in claim 2, wherein each layer contains a different amount of superabsorbent materials.

4. The absorbent structure as claimed in claim 3, wherein the layer having the largest mean pore size contains the lowest amount of superabsorbent material and the layer having the smallest mean pore size contains the highest amount of superabsorbent material.

5. The absorbent structure as claimed in claim 1, wherein the foam material in the different layers may be of different polymers.

6. An absorbent article comprising a liquid permeable topsheet, a liquid impermeable backsheet and an absorbent structure applied therebetween, wherein the absorbent structure is as claimed in claim 1.

7. The absorbent article of claim 6, wherein the absorbent article is a diaper, a pant diaper, an incontinence guard, a sanitary napkin, a wound dressing, or a bed protector.

8. The absorbent structure as claimed in claim 1, wherein the absorbent article is a diaper, a pant diaper, an incontinence guard, a sanitary napkin, a wound dressing, or a bed protector.

9. The absorbent structure as claimed in claim 1, wherein the regenerated cellulose is viscose.

10. An absorbent structure in an absorbent article, the absorbent structure comprising a compressed foam material which expands upon wetting, the foam material comprises a first layer of foam material and a second layer of foam material, wherein the first and second layers have different mean pore sizes, wherein the layers are formed by placing one on top of the other before they are dry so that the layers are integrated so that the foam of the first layer partly penetrates into the foam of the second layer so that there is no clear partitioning line between the layers.

11. An absorbent structure in an absorbent article, the absorbent structure is a compressed foam material which expands upon wetting, the foam material comprises at least two integrated layers having different mean pore sizes, wherein the layers are formed by placing one on top of the other before they are dry so that the layers partly penetrate into each other so that there is no clear partitioning line between the layers, wherein the foam material is regenerated cellulose.

* * * * *